(12) United States Patent
Nagai

(10) Patent No.: US 7,734,338 B2
(45) Date of Patent: Jun. 8, 2010

(54) TREATMENT OF EPILEPSY

(75) Inventor: Yoko Nagai, London (GB)

(73) Assignee: Ultrasis UK Limited, London (GB)

( * ) Notice: Subject to any disclaimer, the term of this patent is extended or adjusted under 35 U.S.C. 154(b) by 590 days.

(21) Appl. No.: 10/739,316

(22) Filed: Dec. 19, 2003

(65) Prior Publication Data

US 2005/0137495 A1 Jun. 23, 2005

(51) Int. Cl.
*A61B 5/00* (2006.01)
(52) U.S. Cl. ........................ 600/547; 128/905
(58) Field of Classification Search ................. 600/547, 600/545; 128/905
See application file for complete search history.

(56) References Cited

U.S. PATENT DOCUMENTS

| | | | | |
|---|---|---|---|---|
| 4,690,142 | A * | 9/1987 | Ross et al. | 607/62 |
| 4,800,893 | A * | 1/1989 | Ross et al. | 600/545 |
| 4,894,777 | A * | 1/1990 | Negishi et al. | 600/558 |
| 5,267,570 | A * | 12/1993 | Preston | 600/544 |
| 5,720,619 | A * | 2/1998 | Fisslinger | 434/336 |
| 5,741,217 | A * | 4/1998 | Gero | 600/547 |
| 5,896,164 | A * | 4/1999 | Orbach et al. | 725/12 |
| 6,026,322 | A * | 2/2000 | Korenman et al. | 600/547 |
| 6,067,468 | A * | 5/2000 | Korenman et al. | 600/547 |
| 6,527,700 | B1 * | 3/2003 | Manico et al. | 600/26 |
| 2003/0109797 | A1 * | 6/2003 | Kim et al. | 600/545 |

FOREIGN PATENT DOCUMENTS

WO WO 93/02622 A1 2/1993
WO WO 9302622 * 2/1993

OTHER PUBLICATIONS

Rosenfeld, JP; "An EEG Biofeedback Protocol for Affective Disorders," 2000, Clin Electroencephalography 2000, p. 7-12☐☐.*

Nagai et al; "Effect of Galvanic Skin Response (GSR) Biofeedback Treatment in Patients with Epilepsy." Jun. 2003 Journal of Neurology Neurosurgery and Psychiatry V74 p. 835.*

Nagai et al; "Clinical Efficacy of Galvanic Skin Response (GSR) Biofeedback on Epilepsy: Randomised Controlled Study." 2003. Epilepsia V44 p. 51.*

BNPA Abstracts: Proceedings of the Head Injury Conference and Annual Meeting of the British Neuropsychiatry Association, the Institute of Child Health, central London, Feb. 12-14, 2003; p. 830-836.*

(Continued)

*Primary Examiner*—Max Hindenburg
*Assistant Examiner*—H. Q. Nguyen
(74) *Attorney, Agent, or Firm*—Breiner & Breiner, L.L.C.

(57) ABSTRACT

Biofeedback training can materially reduce the frequency and/or severity of seizures in sufferers from epilepsy, notably those resistant to treatment by way of therapeutic drugs. By training sufferers to decrease their galvanic skin response, which generally corresponds to an increase in vigilance or awareness, it is found that after such training, the frequency or severity of seizures is reduced, and in particular that by recollecting the training sessions, some patients can reduce the severity of, or avoid, an impending epileptic seizure.

2 Claims, 4 Drawing Sheets

OTHER PUBLICATIONS

Sterman et al: Suppression Of Seizures In An Epileptic Following Sensorimotor EEG Feedback Training; Electroenceph. Clin. Neurophysiology, 33, pp. 89-95, 1972.

Sterman et al: Biofeedback Training Of The Sensorimotor Electroencephalogram Rhythm In Man: Effects On Epilepsy; Epilelsia 15, 1974, pp. 395-416.

Lubar et al: Behavioural Management Of Epileptic Seizures Following EEG Biofeedback Training Of The Sensorimotor Rhythm; Biofeedback and Self Regulation, vol. 1, No. 1, 1976, pp. 77-104.

Fried et al: Behavioural Control Of Intractable Idiopathic Seizures: 1. Self-Regulation Of End-Tidal Carbon Dioxide; Psychosomatic Medicine, vol. 46, No. 4, Jul./Aug. 1984, pp. 315-331.

Tozzo et al: EEG Biofeedback And Relaxation Training In The Control Of Epileptic Seizures; International Journal of Psychophysiology, 6, 1988, pp. 185-194.

Fried et al: Effect Of Diaphragmatic Respiration With End-Tidal $CO_2$ Biofeedback On Respiration, EEG, And Seizure Frequency In Idiopathic Epilepsy; Ann. NY Acad. Sci. 602, 1990, pp. 67-96.

Kotchoubey et al: Modification Of Slow Cortical Potentials In Patients With Refractory Epilepsy: A Controlled Outcome Study; Epilepsia, 2001, 42, pp. 406-416.

G. E. Chatrian et al: DC Changes Recorded Transcranially During "Typical" Three Per Second Spike and Wave Discharges in Man; Epilepsia, 9, pp. 185-209; 1968.

Finley et al: Reduction Of Seizures And Normalisation Of The EEG In Severe Epileptic Following Sensorimotor Biofeedback Training; Preliminary Study. Biol. Psychol. 2, 1975, pp. 189-203.

K. Kuda: The Effect Of Diazepam, Chlorpromazine And Amobarbital On The Contigent Negative Variation; Folia Psychiatrica et Neurologica, Japonica, vol. 31, No. 1, pp. 77-87, 1977.

B. Rockstroh et al: Effects Of The Anticonvulsant Benzodiazepine Clonazepam On Event-Related Brain Potentials In Humans; 1991; Electroencephalography and Clinical Neurophysiology, 78(2); pp. 142-149.

B. Rockstroh et al: Cortical Self-Regulation In Patients With Epilepsies; 1993; Epilepsy Research, 14, pp. 63-72.

* cited by examiner

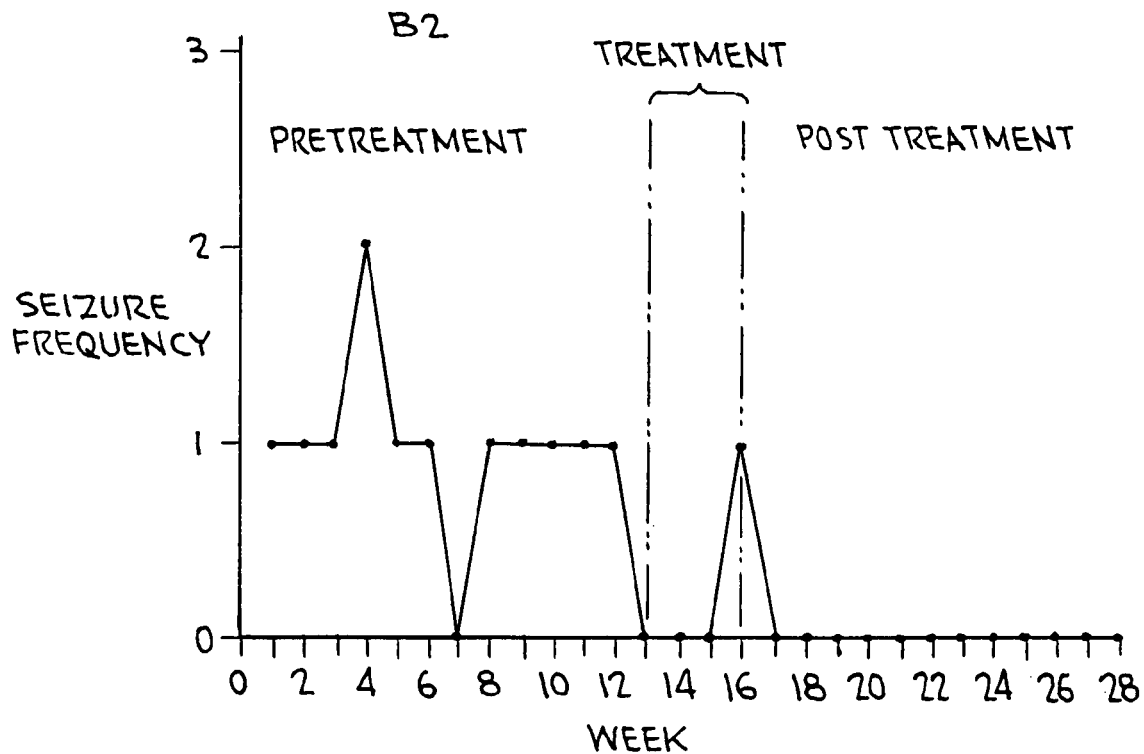
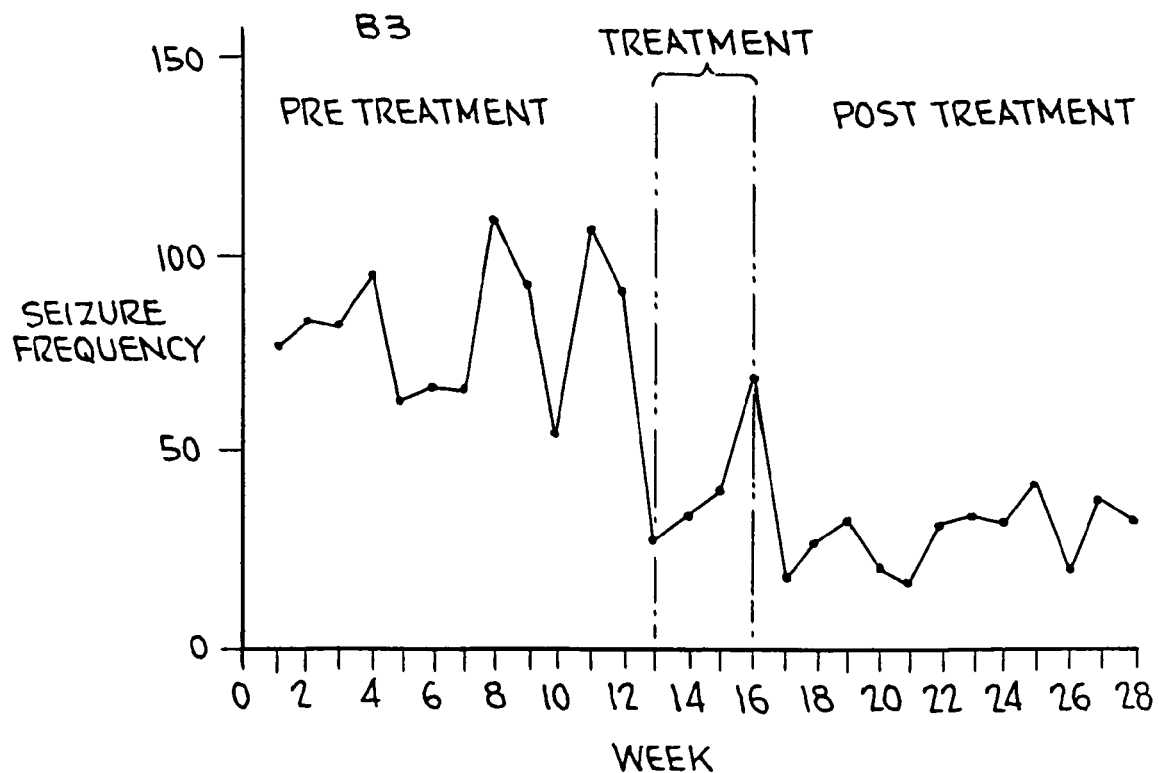

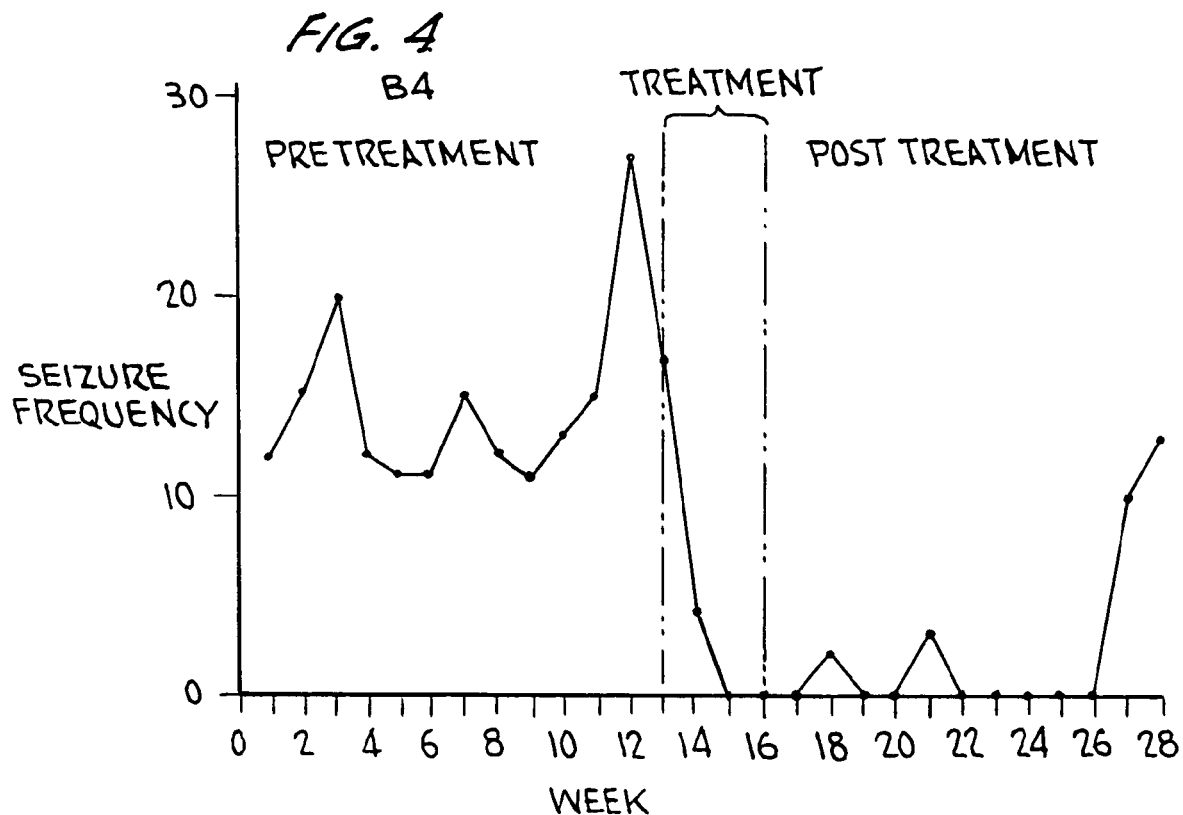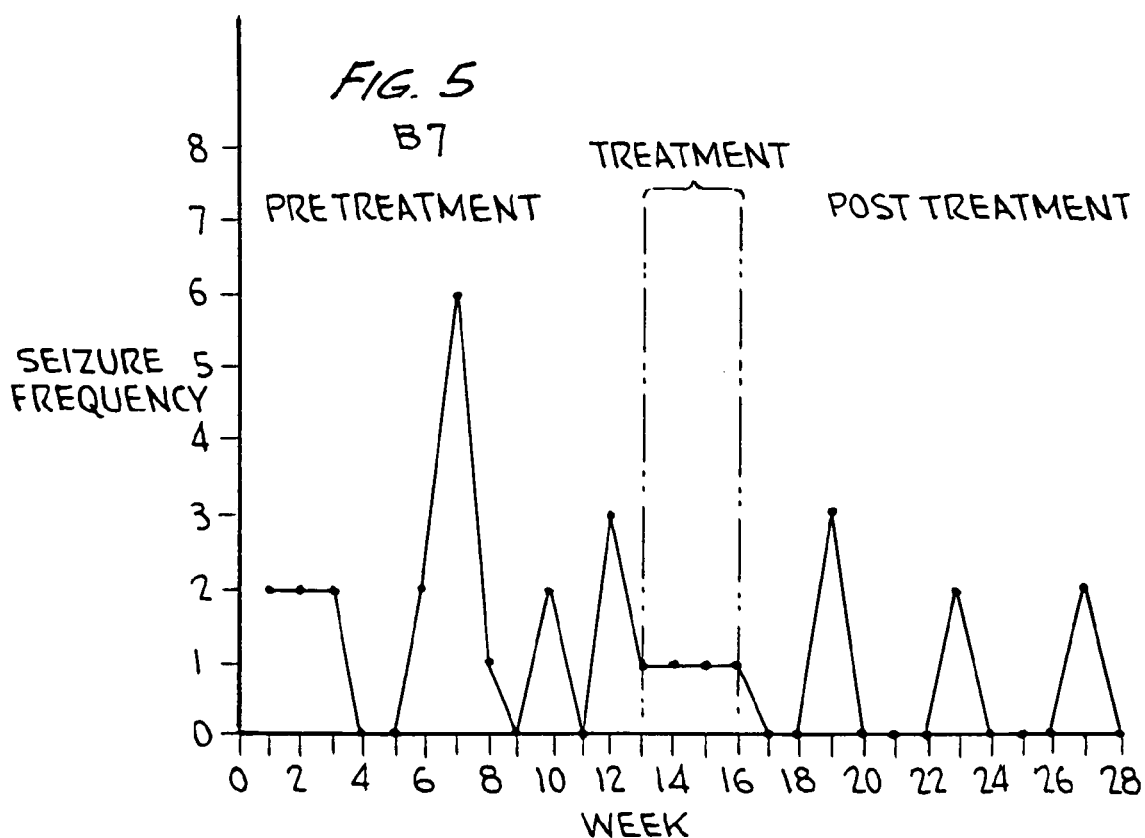

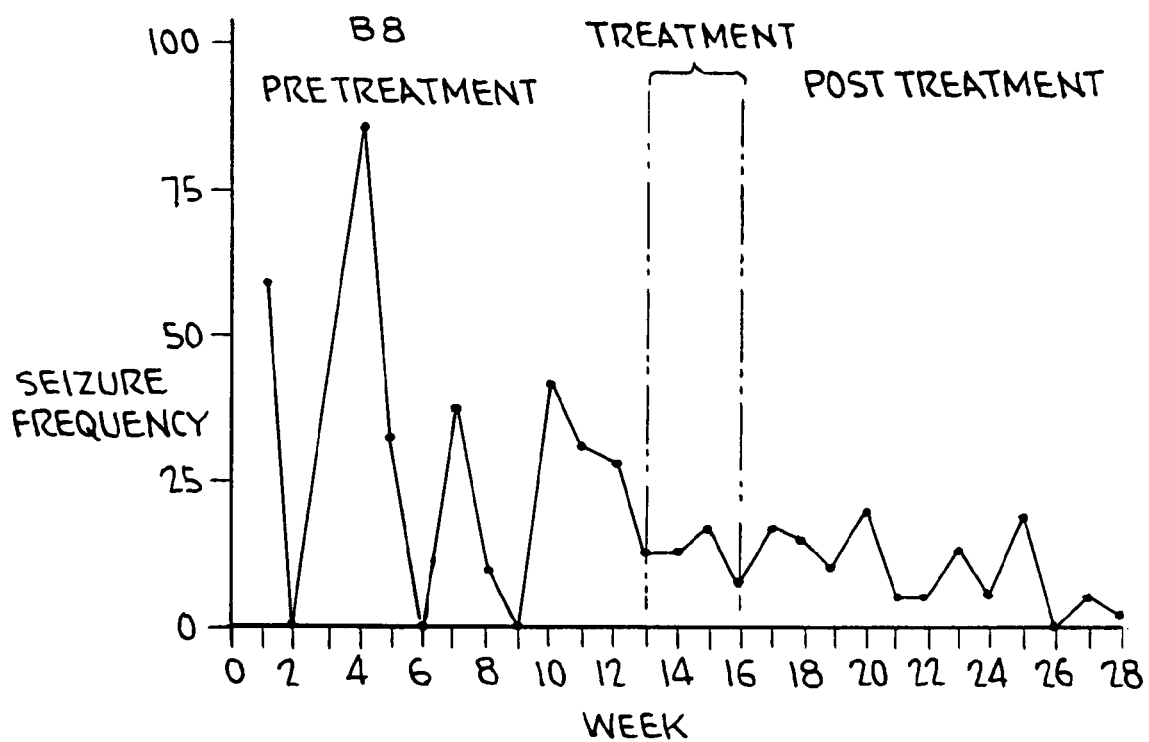
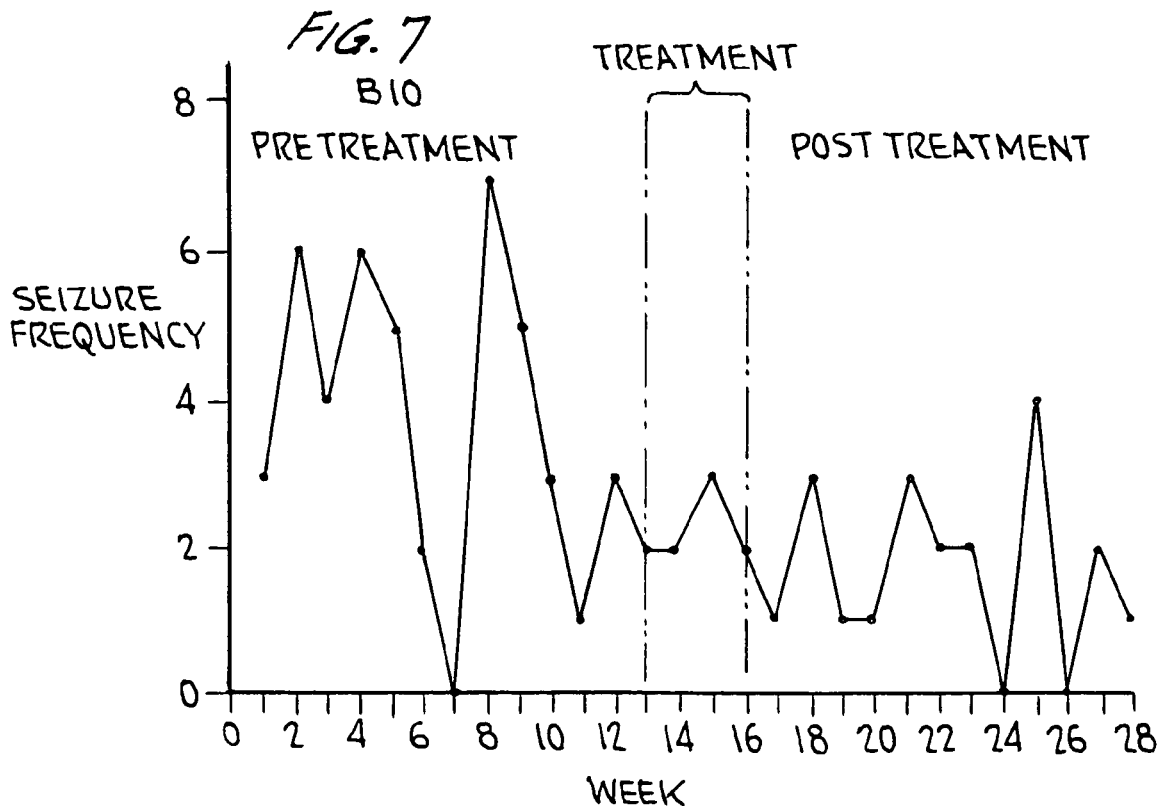

TREATMENT OF EPILEPSY

FIELD OF THE INVENTION

This invention relates to the treatment of sufferers from epilepsy.

BACKGROUND TO THE INVENTION

The effects of epilepsy in sufferers vary widely, the only common feature being the occurrence of epileptic seizures, which are characterised by convulsions and, in severe cases, loss of consciousness. The frequency and severity of such occurrences varies very widely, however, as does the ability of sufferers voluntarily to control them, or to detect an impending occurrence.

The potential dangers of such occurrences have led to very substantial efforts being made to find a cure, or if not a cure then palliative or alleviative measures, for treating epilepsy, and there is a very substantial body of research which has been carried out, which has led to an ability to treat epilepsy in many sufferers, though the effectiveness of such treatment tends also to vary widely.

A large range of synthetic therapeutic drugs is available which affect epilepsy sufferers in different ways. In a substantial proportion of cases, improvements in the management of epilepsy for an individual patient can be achieved, but this tends to be accompanied by considerable side effects and accordingly drug-based management of epilepsy is not seen as a universally positive form of treatment. Indeed, around 30% of all epilepsy sufferers have a resistance to the drugs known for such treatment.

It has long been known that the occurrence of epileptic seizures, and their strength and frequency, correlate with mental state, and accordingly treatment programmes for an individual sufferer may well include mental training or conditioning as well as the physical administration of therapeutic drugs. A number of biofeedback approaches have been suggested for the management of epilepsy. These include different electroencephalographic (EEG) frequencies, cortical potentials and peripheral activity such as respiration (Sterman and Friar, 1972, Suppression of seizures in an epileptic following sensorimotor EEG feedback training. Electroenceph Clin Neurophysiology 33, 89-95; Sterman and McDonald, 1974, Biofeedback training of the sensorimotor electroencephalogram rhythm in man: Effects on epilepsy, Epilepsia 15, 395-416, Finley et al 1975 Reduction of seizures and normalisation of the EEG in severe epileptic following sensorimotor biofeedback training: Preliminary study. Biol. Psychol 2, 189-203; Lubar and Bahler, 1976, Behavioural management of epileptic seizures following EEG biofeedback training of the sensory motor rhythm. Biofeedback Self Regul. 1, 77-104, Fried et al, 1984, Behavioural control of intractable idiopathic seizures: 1. Self-regulation of end-tidal carbon dioxide. Psychosom Med 46, 315-31, Tozzo et al, 1988, EEG biofeedback and relaxation training in the control of epileptic seizures, Int J Psychophysiol 6, 185-94, Fried et al, 1990, Effect of diaphragmatic respiration with end-tidal CO2 biofeedback on respiration, EEG, and seizure frequency in idiopathic epilepsy, Ann NY Acad Sci 602, 67-96; Rockstroh et al, 1993, Cortical self-regulation in patients with epilepsy, Epilepsy Res 14, 63-72, Kotchoubey et al, 2001, Modification of slow cortical potentials in patients with refractory epilepsy: a controlled outcome study. Epilepsia 2001; 42: 406-16).

BRIEF DESCRIPTION OF THE DRAWINGS

FIGS. 2-7 graphically further illustrate results of the clinical trial with respect to six individuals.

GENERAL DESCRIPTION OF THE INVENTION

Figure 1:
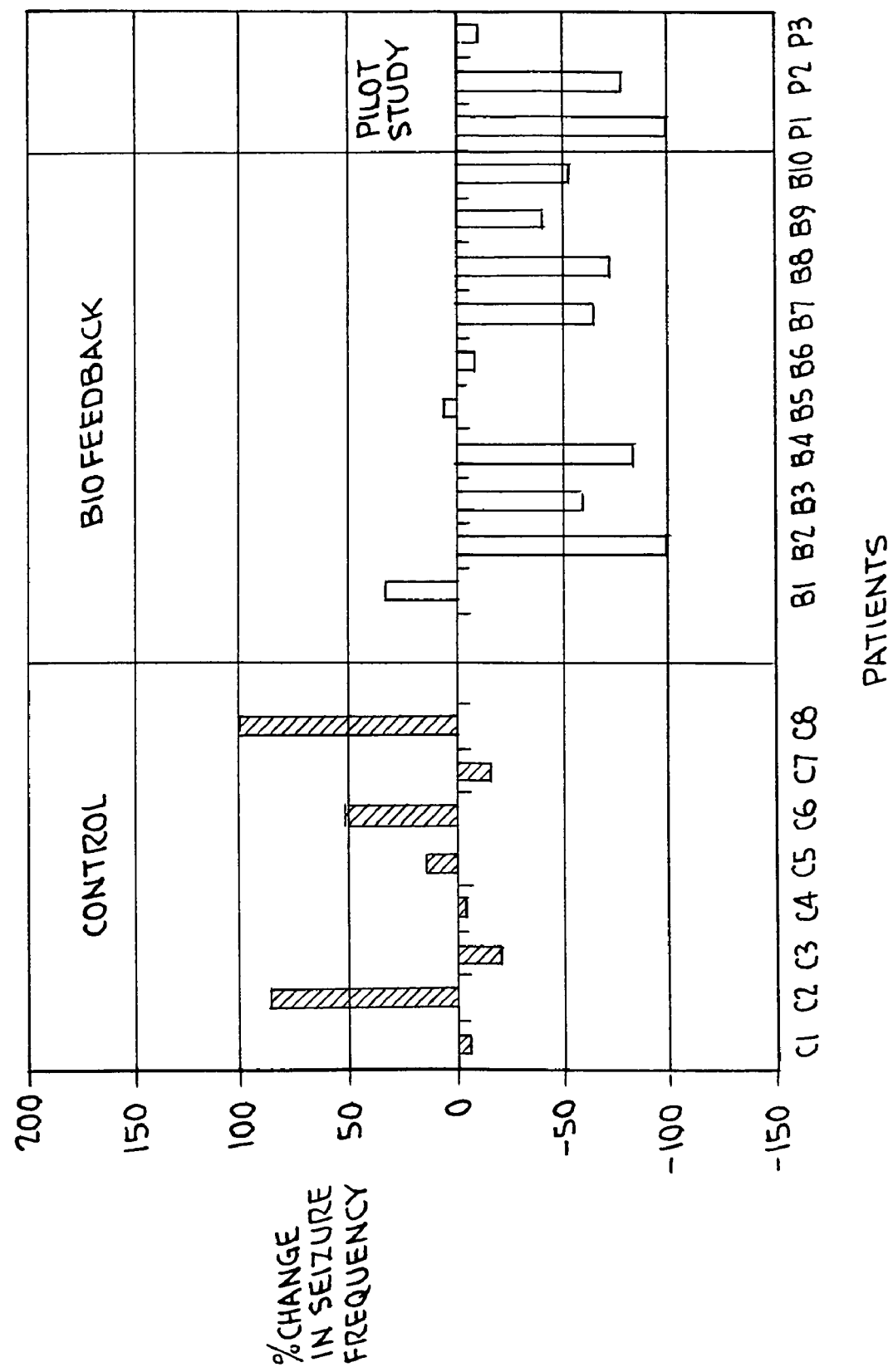
FIG. 1 graphically illustrates the results of a clinical trial utilizing the invention.

It has now been surprisingly discovered that in at least a substantial proportion of these difficult or refractory cases of epilepsy, improvements can be made if they are subjected to biofeedback training which is designed to achieve an increase in vigilance or awareness, as reflected by changes in galvanic skin response (GSR).

It has long been known that galvanic skin response, conventionally measured by the resistance between two electrodes applied spaced apart to the skin, varies with the degree of alertness or relaxation of the subject. This phenomenon has been used in the past to assist in training people to relax. WO 93/02622 describes apparatus for assisting relaxation in which a screen display showing a computer-generated animation is viewed by a user whose galvanic skin response is continuously monitored. As the resistance between the electrodes changes, so the animation may be controlled by a suitable programme to give the user a directly perceptible indication of whether they are becoming more relaxed or more tense, for example by seeing whether an animated fish seen against an underwater landscape is swimming to the left or to the right. After some practice, users learn to be able to control the movement seen on screen to be predominantly in the desired direction corresponding to greater relaxation, i.e. they learn to relax. Physiologically, GSR is an biofeedback training of peripheral sympathetic nervous activity, reflecting peripheral autonomic changes.

According generally to the present invention there is provided a method of treating a sufferer from epilepsy by way of biofeedback training, in which in each of a series of training sessions at least the galvanic skin response of the sufferer is monitored, while an animated display is viewed by the sufferer, and where the sufferer is requested, during each session, to influence the animation in a way which corresponds to a decrease in skin resistance.

It has been found that after such treatment a substantial improvement in the condition of sufferers from epilepsy can be achieved, particularly in those cases which appear to be resistant to treatment with any of the currently available range of anti-epileptic drugs. It is believed that one way in which the GSR biofeedback acts to reduce epileptic seizures is that it acts to effect cortical potential changes. It is already known that the cortical potential change is crucial for seizure occurrences (Chatrian G. E., Somasundaran M. and Tassinari C. A. (1968) DC-changes recorded transcranially during "typical" 3 sec spike-wave discharges in man. Epilepsia 9: 185-209; Kuda K. (1977) The effect of diazepam, chlorpromazine and amovarbital on the contingent negative variation. Folia Psychiatr Neurol Jpn, 31(1): 77-87; Rockstroh B., Elbert T., Lutzenberger W. and Altenmuller E. (1991) Effect of the anticonvulsant benzodiazepine clonazepam on event-related brain potentials in humans. Electroencephalogr Clin Neurophysiol, 78(2): 142-149; Rockstroh B., Elbert T., Birbaumer N., Wolf P., Duchtingroth A., Reker M., Daum I., Lutzenberger W. and Dichgangs J., (1993) Cortical self-regulation in patients with epilepsy, Epilepsy Research, 14: 63-72).

The treatment is preferably carried out as a series of regular sessions spaced over a period of 20 to 60 days, each session lasting at least 10 minutes, but usually no longer than 40 minutes. During each session the subject tries to follow the instruction to make the animation reflect a decrease in skin resistance by increasing their own vigilance or alertness, but preferably without recourse to physical activity, merely by mental activity.

The effects of such training do not fade rapidly. In some cases there can be effective permanent improvement, while in others it may be desirable to repeat a training procedure, but the intervals appropriate for such repetition may vary widely from one patient to another. However, in most cases the effect is well-maintained: the period of several months can elapse after the treatment during which both the frequency and severity of seizures is reduced often lasts for several months. The reduction in frequency is thought to stem, in part, from measurable changes in the brain which are not consciously perceptible by the sufferer. In addition, however, the severity of seizures is thought to be decreased at least in part voluntarily by conscious effort on the part of the sufferer who, when they feel a seizure is imminent, can call back to mind the memory of the training sessions, which seems to decrease the severity of the seizure, or indeed avoid its occurrence.

The simple biofeedback technique used involves the use of suitable biofeedback apparatus, preferably incorporating low power consumption compact visual display devices. This enables epilepsy sufferers to be provided with apparatus for use in carrying out the method of the invention which can be used at home and thus easily and quickly deployed when desired by the sufferer with a view to improving their condition.

As can be easily appreciated, such apparatus may be analogous to the apparatus used in a clinical setting, e.g. in an outpatient department, to provide the sufferer with the initial training in management of their condition according to the invention. In the case of apparatus for use in a clinical setting, however, the apparatus may be designed to record other patient data during training sessions with a view to improved monitoring and diagnosis.

Indeed, in a clinical setting, the physician may be able to assess the susceptibility of any particular sufferer to changes in their physiological, psychological or emotional state, and tailor both biofeedback training sessions and downstream online monitoring using communications technology, to match the needs of the sufferer in question.

The following details of two investigations will illustrate the invention:

Pilot Clinical Trial

Three epilepsy sufferers were available, all experiencing at least two or three seizures a month, and having a history of no or poor response to anti-epileptic drug therapy, and who were not apparently suffering from mental illness.

Baseline seizure frequency was measured and recorded for three months. At the beginning of the fourth month, the three sufferers took part in biofeedback training sessions three times a week using apparatus as described in WO 93/02622, and with an animation sequence programmed into tho PC showing a fish swimming to left or right against a background scene. All three were asked by being alert to try to make the fish swim to the right, preferably without making physical movements, and without closing their eyes. The thrice-weekly sessions were carried out for four weeks and then discontinued. Throughout the time, and for the following three months, a record of seizure occurrences was kept for all three.

It was found that the seizure frequency was clearly reduced in the case of two of the three sufferers, though no significant change was found in the case of the third.

Wider Clinical Trial

This study sought to investigate the effects demonstrated by the pilot, but on a larger scale to provide same reliability. It was designed as a randomized control trial and carried out using the standard procedures for such trials. To start with, a group of drug refractory epilepsy sufferers was set up. The conditions of entry to the group were that the sufferer had to be between the ages of 16 and 60, to have suffered epileptic seizures for two years or more and at a rate of at least two to three seizures per month, and to have been on stable medication. Eighteen epilepsy sufferers who met these criteria were asked to participate in a seven month experiment to test a new treatment and, on giving informed consent, were randomly assigned to a group which was to receive actual GSR feedback and a group which was to act as a sham control group.

A preliminary analysis following the random allocation of the eighteen sufferers into a group of ten and a group of eight demonstrated that the two groups could be considered essentially identical, i.e. there was no statistically significant difference between the two groups, both showing a spread of age and severity and type of their epileptic condition.

Each of the participants kept a seizure diary for three months to establish baseline seizure frequency and then each was trained in biofeedback techniques (or exposed to sham biofeedback) over twelve sessions spread over a period of one month. The thrice-weekly sessions each lasted 30 minutes and in each case the sufferer was reminded of the task they were set, which was to make the computer-generated animation of a swimming fish move in a particular direction. In the case of ten of the sufferers, they were genuinely able to influence the movement of the fish on the screen by varying their alertness causing a change in GSR, this being achieved using a commercial biofeedback programme and its associated electrodes and sensors available commercially from Ultrasis UK Limited under the designation Inner Tuner.

Those of the other group in the sham control group were given the same instructions as those in the other group, but the screen display shown to each of them was a pre-recorded animation sequence where the movement of the fish was random. None of the sufferers in the sham control group gave any indication of realizing that they were in that group, although none actually experienced any reduction in seizure frequency during the period of the twelve sessions. In contrast, six of the ten sufferers in the group exposed to genuine biofeedback experienced a reduction in seizure frequency before the end of the twelve sessions to 50% or less of their baseline frequency.

Thereafter, all 18 sufferers kept a seizure diary for a further three months and, at the end of that period, the data was collected from the diaries and analysed.

On analysing the data at the end of the seven month trial, there was a substantial difference in seizure reduction between the groups. In the group which received genuine biofeedback, there was a statistically significant decrease in seizure frequency. Of the ten patients in that group, six showed more than a 50% reduction in seizure frequency, the mean percentage change being −49.26%. Two patients even became virtually seizure free.

In contrast, in the sham control group of eight patients, there was no statistically significant reduction in the seizure frequency. These results are shown graphically in FIG. 1.

It is particularly noteworthy that, in the case of six of the individuals, there was a good response to treatment over the seven month period and this is shown in FIGS. 2-7.

I claim:

1. A method of treating a sufferer of epilepsy by way of biofeedback training to reduce the frequency and/or severity of seizures of the sufferer, comprising the steps of: in each of a series of training sessions, viewing by the sufferer an animated display, monitoring at least galvanic skin response of the sufferer while the sufferer is viewing said animated display, and instructing the sufferer to influence said animated display in a way which corresponds to a decrease in skin resistance, whereby mental arousal of the sufferer increases to decrease the skin resistance to influence the animated display, to improve the condition of the sufferer of epilepsy by reducing the frequency and/or severity of seizures.

2. A method according to claim 1 wherein the training sessions are between 10 and 20 in number, spaced over a period of 10 to 60 days and each session lasting between 10 and 40 minutes.

* * * * *